United States Patent
Liao et al.

(10) Patent No.: US 10,957,037 B2
(45) Date of Patent: Mar. 23, 2021

(54) SMART IMAGING USING ARTIFICIAL INTELLIGENCE

(71) Applicant: Siemens Healthcare GmbH, Erlangen (DE)

(72) Inventors: Rui Liao, West Windsor Township, NJ (US); Erin Girard, New York, NY (US); Shun Miao, Princeton, NJ (US); Xianjun S. Zheng, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 245 days.

(21) Appl. No.: 15/697,559

(22) Filed: Sep. 7, 2017

(65) Prior Publication Data

US 2019/0073765 A1 Mar. 7, 2019

(51) Int. Cl.
| | |
|---|---|
| *G06K 9/00* | (2006.01) |
| *G06T 7/00* | (2017.01) |
| *G06T 5/00* | (2006.01) |
| *G06N 3/08* | (2006.01) |
| *A61B 6/03* | (2006.01) |

(52) U.S. Cl.
CPC .............. *G06T 7/0012* (2013.01); *G06N 3/08* (2013.01); *G06T 5/002* (2013.01); *G06T 5/003* (2013.01); *G06T 7/0002* (2013.01); *A61B 6/032* (2013.01); *G06T 2207/30004* (2013.01); *G06T 2207/30168* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 6,412,980 B1 | 7/2002 | Lounsberry et al. | |
| 6,988,074 B2 | 1/2006 | Koritzinsky et al. | |
| 7,685,262 B2 | 3/2010 | Choubey et al. | |
| 8,529,446 B2 | 9/2013 | Schmidt et al. | |
| 9,323,891 B1 | 4/2016 | Fram | |
| 2006/0241455 A1 | 10/2006 | Shvarts | |
| 2016/0364862 A1* | 12/2016 | Reicher | G06F 19/00 |
| 2017/0213007 A1* | 7/2017 | Moturu | G06F 19/00 |
| 2018/0018757 A1* | 1/2018 | Suzuki | G06T 3/4046 |
| 2018/0144214 A1* | 5/2018 | Hsieh | G06K 9/6265 |

* cited by examiner

Primary Examiner — Wei Wen Yang

(57) ABSTRACT

Systems and methods are provided for determining a set of imaging parameters for an imaging system. A selection of an image is received from a set of images. A modification of certain quality measures is received for the selected image. The modified selected image is mapped to a set of imaging parameters of an imaging system based on the certain quality measures using a trained Deep Reinforcement Learning (DRL) agent.

20 Claims, 5 Drawing Sheets

SMART IMAGING USING ARTIFICIAL INTELLIGENCE

BACKGROUND OF THE INVENTION

The present invention relates generally to medical imaging systems, and more particularly to automatically determining parameters for medical imaging systems using an intelligent artificial agent to optimize image quality for a user.

Medical imaging systems are typically used by doctors and other medical professions for clinical analysis and medical intervention procedures. The desired quality of the images generated by the medical imaging systems depends on the subjective preferences of the doctor. For example, different doctors may prefer different amounts of sharpness, fuzziness, blurring, noise, dynamic range, contrast, smoothness, brightness, etc. in the images.

Conventionally, medical imaging systems are manually configured by adjusting its imaging parameters according to the preferences of the doctor, the conditions of the patient, and the medical procedure being performed. Such manual configuration of such conventional medical imaging systems is labor intensive, time consuming, and expensive due to the numerous possible imaging parameters and their non-linear relationship to the resulting quality of the medical images.

BRIEF SUMMARY OF THE INVENTION

In accordance with one embodiment, systems and methods are provided for determining a set of imaging parameters for an imaging system. A selection of an image is received from a set of images. A modification of certain quality measures is received for the selected image. The modified selected image is mapped to a set of imaging parameters of an imaging system based on the certain quality measures using a trained Deep Reinforcement Learning (DRL) agent.

In accordance with one embodiment, a new image is generated using the imaging system configured with the set of imaging parameters. The subject being imaged may be continually monitored and the modified selected image may be mapped to an updated set of parameters of the imaging system using the trained DRL agent based on the monitoring.

In one embodiment, the modified selected image is mapped to the set of parameters of the imaging system by generating a resulting image using the imaging system configured with the set of imaging parameters, comparing certain quality measures of the resulting image with the certain quality measures of the modified selected image, and mapping the resulting image to an updated set of imaging parameters of the imaging system using the trained DRL agent.

The generating, the comparing, and the mapping the resulting image may be iteratively repeated using the respective updated set of imaging parameters until the comparing satisfies a threshold. In one embodiment, comparing the certain quality measures of the resulting image with the certain quality measures of the modified selected image may be performed by quantifying values of the certain quality measures for the resulting image (e.g., using deep learning based methods) and comparing the quantified values of the certain quality measures for the resulting image with the certain quality measures of the modified selected image.

In one embodiment, the certain quality measures are determined from a set of quality measures for one or more users based on actions of the one or more users on one or more given images using a deep inverse reinforcement learning (DIRL) based method. For example, the actions may include selecting an image, weighting an image, modifying an image, etc. The values of the set of quality measures for the one or more given images may be quantified using a trained deep learning based method.

In one embodiment, the one or more quality measures include at least one of sharpness, fuzziness, blurring, noise, dynamic range, contrast, smoothness, and brightness.

These and other advantages of the invention will be apparent to those of ordinary skill in the art by reference to the following detailed description and the accompanying drawings.

DETAILED DESCRIPTION

The present invention generally relates to determining parameters of medical imaging systems to optimize image quality for a user. Embodiments of the present invention are described herein to give a visual understanding of methods for determining parameters of medical imaging systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Further, it should be understood that while the embodiments discussed herein may be discussed with respect to medical imaging systems for imaging a patient, the present invention is not so limited. Embodiments of the present invention may be applied for determining parameters for configuring any imaging system (e.g., cameras and video recording devices) for imaging any subject.

Figure 1:
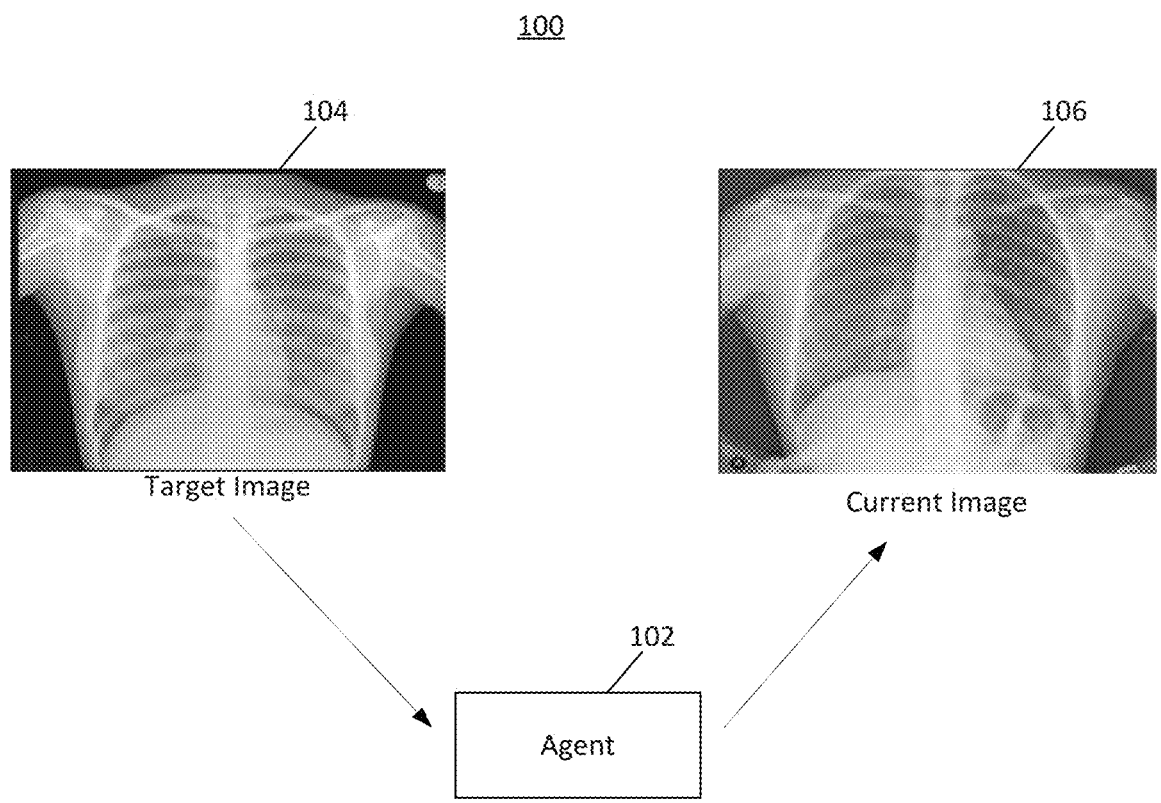
FIG. 1 shows an exemplary high level workflow for determining parameters of a medical imaging system for optimizing image quality for a user, in accordance with one or more embodiments.

FIG. 1 shows a high level workflow 100 for determining parameters of a medical imaging system for optimizing image quality for a user, in accordance with one or more embodiments. In workflow 100, intelligent artificial agent 102 receives a user selection of a target image 104 from a set of images. Target image 104 may be selected by a doctor, medical professional, or any other user based on his or her subjective preferences. Target image 104 may be further modified by the user based on his or her subjective preferences. Agent 102 applies machine learning algorithms trained to map the modified target image 104 to a set of parameters of a medical imaging system. The medical imaging system may be configured with the determined set of parameters to generate a current image 106 having a quality similar to that of the modified target image 104.

Figure 2:
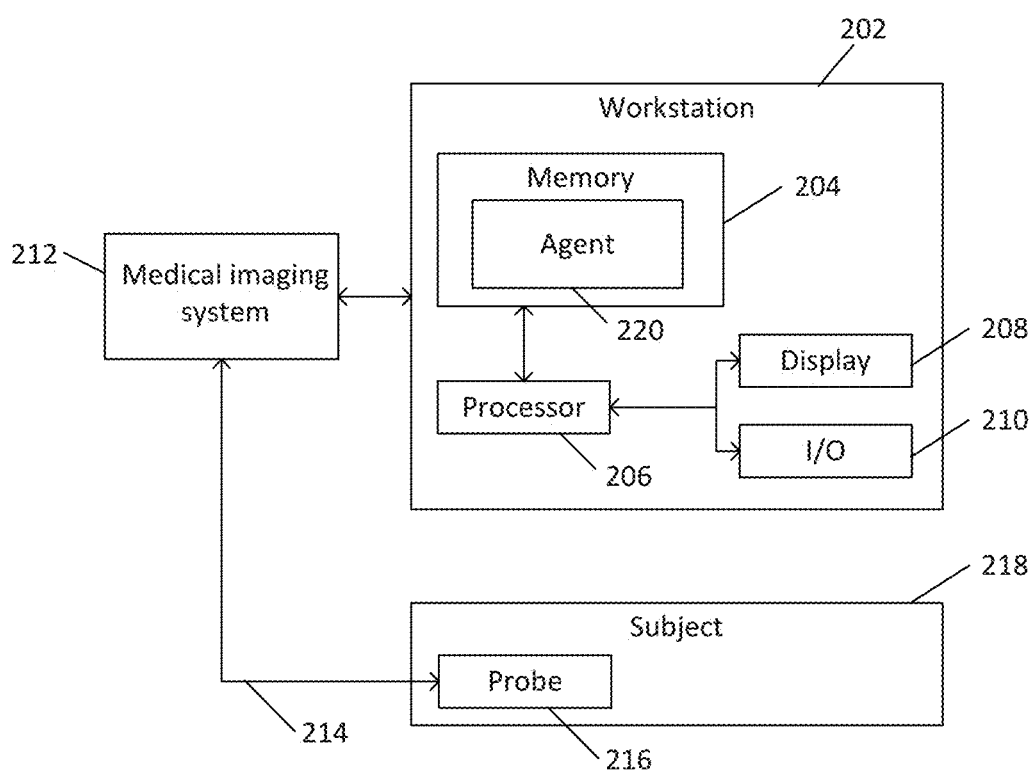
FIG. 2 shows an exemplary system configured for determining a set of parameters of a medical imaging system for optimizing image quality for a user, in accordance with one or more embodiments.

FIG. 2 shows a system 200 configured for determining a set of parameters of a medical imaging system for optimizing image quality for a user, in accordance with one or more embodiments. System 100 includes workstation 202, which may be used for assisting a user (e.g., a doctor, clinician, or any other medical professional) during a procedure, such as, e.g., a patient examination. Workstation 202 includes one or more processors 206 communicatively coupled to memory 204, display device 208, and input/output devices 210. Memory 204 may store a plurality of modules representing functionality of workstation 202 performed when executed on processor 206. It should be understood that workstation 202 may also include additional elements, such as, e.g., a communications interface.

In one embodiment, an intelligent artificial agent 220 is implemented on workstation 202 to determine parameters of medical imaging system 212 for optimizing image quality for a user. Agent 220 may be implemented as computer program instructions (e.g., code), which may be loaded into memory 204 and executed by processor 206. In one embodiment, agent 220 implemented on workstation 202 in FIG. 2 is agent 102 in FIG. 1.

Workstation 202 may assist the clinician in imaging subject 218 (e.g., a patient) for a medical procedure. While subject 218 is described herein as being a patient, it should be understood that subject 218 may include any object (e.g., any person, place, or thing). Workstation 202 may receive medical imaging data generated by medical imaging system 212. Medical imaging system 212 may be any modality, e.g., magnetic resonance imaging (MRI), computed tomography (CT), ultrasound (US), single-photon emission computed tomography (SPECT), positron emission tomography (PET), or any other suitable modality, or any combination of modalities.

In some embodiments, medical imaging system 212 may employ one or more probes 216 for imaging subject 218. Probe 216 may be instrumented with one or more devices (not shown) for performing the medical procedure. The devices instrumented on probe 216 may include, for example, imaging devices, tracking devices, insufflation devices, incision devices, and/or any other suitable device. Medical imaging system 212 is communicatively coupled to probe 216 via connection 214, which may include an electrical connection, an optical connection, a connection for insufflation (e.g., conduit), or any other suitable connection.

The desired quality of the images generated by medical imaging system 212 depends on the subjective preferences of the user, and may also be based on subject 218 and the medical procedure being performed. To generate images having a quality according to the subjective preferences of the user from medical imaging system 212, parameters of medical imaging system 212 must be set before an exam or procedure is performed. For example, in one embodiment, where medical imaging system 212 is an MRI imaging system, the parameters of the MRI imaging system may include repetition time (TR) and echo time (TE). In another example, the parameters may include energy level for computed tomography (CT), x-ray, and conebeam CT imaging systems. Post-processing parameters may include, e.g., imaging smoothing, image sharpening, and noise reduction.

Advantageously, agent 220 applies machine learning methods (e.g., deep learning based methods) to map a target image, selected and modified in accordance with the user's subjective preferences, to a set of imaging parameters for medical imaging system 212. In this manner, medical imaging system 212 configured with the determined set of imaging parameters may generate new images having a quality in accordance with the subject preferences of the user. Agent 220 in accordance with embodiments of the invention thus provides for improvements in computer related technology by automatically tuning the imaging parameters of medical imaging system 212 to thereby generate new images optimized according to the subjective preferences of the user. Agent 220 avoids the time consuming, labor intensive, and ad hoc manual configuration of the imaging parameters of medical imaging system 212, thereby reducing time and expense in configuring medical imaging system 212.

Figure 3:
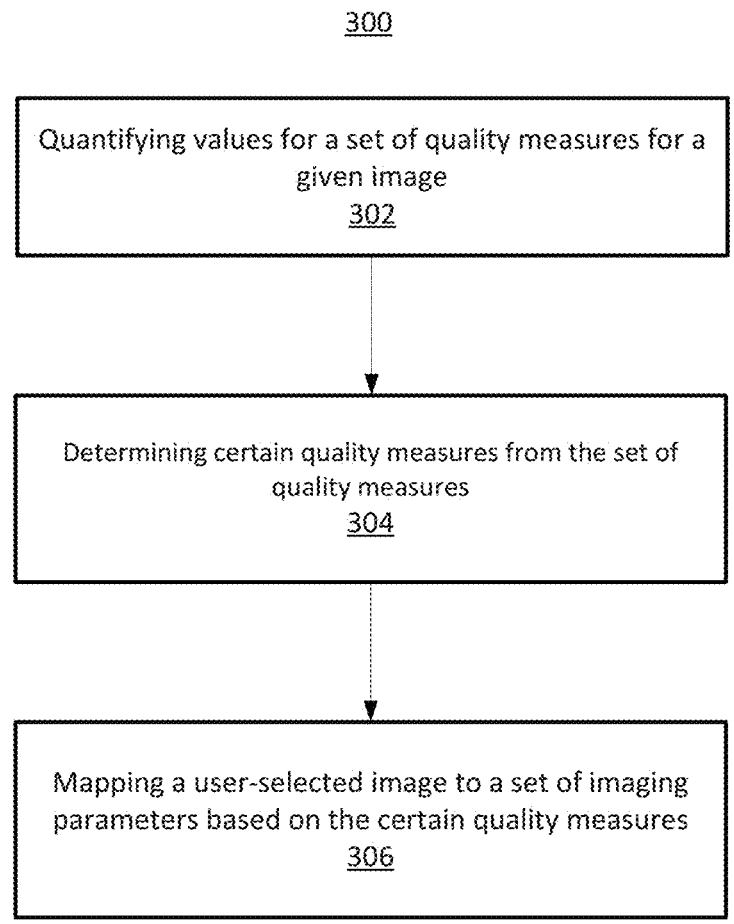
FIG. 3 shows a method for determining a set of imaging parameters of a medical imaging system for optimizing image quality for a user, in accordance with one or more embodiments.

FIG. 3 shows a method 300 for determining a set of imaging parameters of a medical imaging system for optimizing image quality for a user, in accordance with one or more embodiments. Method 300 will be discussed with respect to system 200 of FIG. 2. In one embodiment, agent 220 implemented on workstation 202 of FIG. 2 performs the steps of method 300 of FIG. 3.

At step 302, values for a set of quality measures are quantified for one or more given images. The quantified values for the set of quality measures represent the subjective or perceptual appearance for the given image. For example, the quality measures may include various levels of sharpness, fuzziness, blurring, noise, dynamic range, contrast, smoothness, brightness, and/or any other image attribute or combinations of image attributes. The given image may be any suitable image. In one embodiment, the given image is a medical image (e.g., an x-ray image or magnetic resonance image) of a target region on interest with desired quality measures (e.g., image contrast, brightness, noise level, and field of view). In one embodiment, step 302 is a pre-processing step that is performed once.

Values for the set of quality measures for the given image may be quantified using deep-learning based methods to map the given image to the values for the set of quality measures. A deep-learning network is trained from a database of training images associated with various qualities. The training images are labelled with a corresponding values (or levels) for each quality measure in the set of quality measures. In one embodiment, training images are patient images labeled by applying mathematical definitions or calculations and confirmed or modified by users (e.g., experts). In another embodiment, the training images may alternatively or additionally be synthetic images which are generated by simulating the medical imaging system with known values for the set of quality measures. Once the deep-learning network is trained, it is applied to the given image to quantify the set of quality measures.

At step 304, certain quality measures are determined or identified from the set of quality measures. The certain quality measures may be the quality measures in the set of quality measures that are the most influential. In one embodiment, step 304 is a pre-processing step that is performed once for a group of users to provide for a general set of the certain quality measures for a given type of image modality (e.g., x-ray, ultrasound, computed tomography, magnetic resonance imaging, etc.). In another embodiment, step 304 may be performed for each particular user to provide for a specific set of the certain quality measures for that particular user. In this embodiment, the user may be the same user associated with step 306.

The certain quality measures may be determined using, e.g., a deep inverse reinforcement learning (DIRL) based method. In DIRL, no reward function is provided. The goal of DIRL is to learn the reward function by observing the behavior of an agent assumed to be behaving optimally (i.e., in accordance with a policy). The reward function represents a policy for performing an action in view of a goal. The reward function assigns a reward for each action based on the effect of that action on the goal. For example, a higher reward (positive reward) is assigned for actions that lead towards the accomplishment of the goal while a lower reward (negative reward) is assigned to actions that do not lead towards the accomplishment of the goal.

The DIRL based method observes actions of the user (or group of users) to learn the reward function. The user actions may include user modifications of the quantified values of the given images according to the subjective preferences of the user or users. In some embodiments, the user actions may additionally or alternatively include user selections of the quantified given images from a set of images, weighting the quantified given images according to the subjective preferences of the user, or any other suitable user action. The modifications of the quantified values of the given images are of one or more quality measures of the set of quality measures, e.g., sharpness, fuzziness, blurring, noise, dynamic range, contrast, smoothness, brightness, and/or any other image attribute of the selected image.

At step 306, a user-selected image is mapped to a set of imaging parameters based on the certain quality measures. In one embodiment, step 306 is performed by performing method 400 of FIG. 4.

Figure 4:
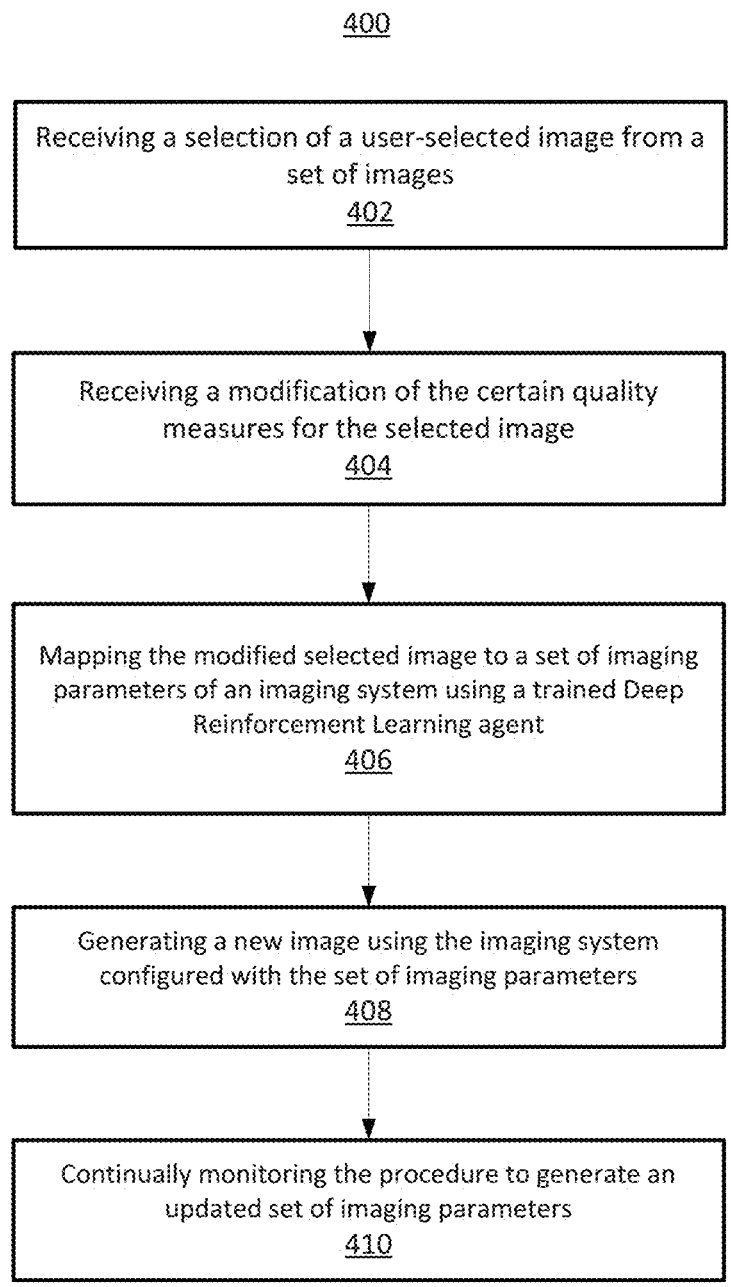
FIG. 4 shows a method for mapping an image to a set of imaging parameters.

FIG. 4 shows a method 400 for mapping a user-selected image to a set of imaging parameters of a medical imaging system, in accordance with one or more embodiments. Accordingly, the medical imaging system configured with the set of imaging parameters generates images with a quality measure in accordance with the subjective preferences of the user.

At step 402, a selection of an image is received from a user from a set of images. The user may be any user, such as, e.g., a doctor or a medical professional. The selection may be received using display 208 and/or input/output device 210 of FIG. 2. The set of images may include one or more images of various qualities stored in memory 204. For example, the various qualities of the set of images may include various levels of sharpness, fuzziness, blurring, noise, dynamic range, contrast, smoothness, brightness, and/or any other image attribute or combinations of image attributes. The selection of the image from the set of images reflects or is based on the subjective preferences of the user. In one embodiment, the selection of the image is also based on the procedure being performed and the subject 218 (e.g., the patient) of the procedure. For example, if an MR scan is being acquired to detect lesions, then the image may be selected from the set of images based on its ability to detection lesions. While the image quality may traditionally be considered poor in this example, it could be optimized for the diagnostic task that the scan is being performed for.

The set of images may include actual medical images of patients acquired from medical imaging system 212 or any other suitable medical imaging system of a same or different modality (e.g., CT, MR, x-ray, ultrasound, PET, etc.). The set of images may be acquired from the same patient as new images generated from medical imaging system 212 during an online phase, and may be generated at different times and from different patients. The set of images can be obtained by receiving the images directly from medical imaging system 212 or by loading previously acquired images from a storage or memory of a computer system. In some embodiments, the set of images can include synthetic images which are generated by simulating the medical imaging system.

In one embodiment, a plurality of images may be selected from the set of images by the user. The user may assign or associate a weight to each respective selected imaging indicating the subjective preferences of the user for that respective selected image.

At step 404, modifications of the selected image are received from the user according to the subjective preferences of the user. The modifications of the selected image may include edits or refinements of the selected image that alter the appearance of the selected image according to the most influential quality measures. In one embodiment, the certain quality measures that are modified at step 404 are the certain quality measures (e.g., the most influential quality measures) determined in step 304 of FIG. 3. For example, the certain quality measures may include sharpness, fuzziness, blurring, noise, dynamic range, contrast, smoothness, brightness, and/or any other image attribute of the selected image.

At step 406, the modified selected image is mapped to a set of parameters of medical imaging system 212 using a trained Deep Reinforcement Learning (DRL) agent. The DRL agent is trained in an offline or training stage to generate the set of parameters (i.e., one or more parameters) for configuring medical imaging system 212 such that new images generated by medical imaging system 212 so configured have a quality in accordance with (i.e., similar to) the subjective preferences of the user. In one embodiment, the DRL agent employs a Deep Neural Network (DNN) trained using a supervised DRL technique. Reinforcement Learning (RL) is a type of machine learning in which a software based artificial agent uses reward feedback to automatically learn ideal behavior in a specific context and for a specific task. In DRL, which combines DNNs with RL, a policy learning process is formulated as an RL problem and the action-value function is estimated as an iterative update. In DRL, the training of the agent is typically unguided and the agent is free to evolve in its environment according to its current policy estimate.

In an advantageous embodiment of the present invention, the DRL training of the DNN is supervised based on training images annotated with known ground truth parameters of medical imaging systems. The training images may be imaging data of a same or different subject, taken by a same or different medical imaging system that generates the imaging data in the online phase. In one embodiment, the training images may include synthetic imaging data generated by simulating a medical imaging system. The training images may be annotated with a policy goal and actions (that lead towards or away from the policy goal). The DRL agent is trained by letting the agent repeatedly take actions to adjust the imaging parameters and collect the produced rewards. During these actions, the agent establishes the connection between the imaging parameters and the associated rewards. In one embodiment, the reward function used in the training phase may be, e.g., the sum of the squared difference between the quality measures of the current image and the target image, and its variations. Once the agent is trained, it can be applied to adjust the imaging parameter on a new image to maximize the reward.

In one embodiment, the DRL agent maps the modified selected image to the set of imaging parameters and generates a resulting image using the determined set of parameters. The certain quality measures of the resulting image are then compared to the certain quality measures of the modified selected image. For example, the certain quality measures of the resulting image may be quantified using deep learning based methods and compared with the known values of the certain quality measures of the modified selected image. If the comparison of the certain quality measures of the resulting image and the modified selected image does not satisfy a (e.g., predetermined) threshold, the DRL agent maps the resulting image to a new set of imaging parameters. This step may be iteratively repeated until the threshold is satisfied, indicating that the set of imaging parameters generate images that have sufficiently similar certain quality measures as the modified selected image.

In one embodiment, the DRL agent maps the modified selected image to the set of imaging parameters in a single step, for a given size or anatomy of subject 218.

At step 408, a new image is generated using the medical imaging system configured with the determined set of imaging parameters. The new image will advantageously have a quality in accordance with (e.g., similar to) the user's subject preferences.

At step 410, the medical procedure is continually monitored for changes to generate an updated set of imaging parameters. For example, conditions such as, e.g., size of subject 218, the procedure being performed, the devices being used) may alter the set of parameters for generating optimized images for the user.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 3 and 4. Certain steps of the methods described herein, including one or more of the steps of FIGS. 3 and 4, may be performed by a server or by another processor in a network-based cloud-computing system. Certain steps of the methods described herein, including one or more of the steps of FIGS. 3 and 4, may be performed by a client computer in a network-based cloud computing system. The steps of the methods described herein, including one or more of the steps of FIGS. 3 and 4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 3 and 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
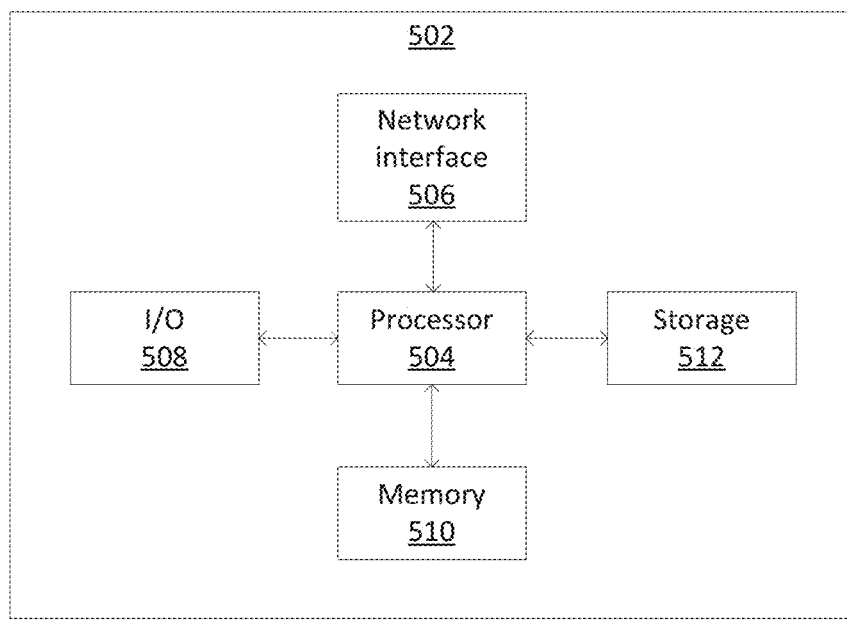
FIG. 5 shows a high-level block diagram of a computer for determining a set of parameters of a medical imaging system for optimizing image quality for a user, in accordance with one or more embodiments.

A high-level block diagram 500 of an example computer that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method steps of FIGS. 3 and 4 can be defined by the computer program instructions stored in memory 510 and/or data storage device 512 and controlled by processor 504 executing the computer program instructions. For example, the computer program instructions can be implemented as computer executable code programmed by one skilled in the art to perform the method steps of FIGS. 3 and 4. Accordingly, by executing the computer program instructions, the processor 504 executes the method steps of FIGS. 3 and 4. Computer 504 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

Any or all of the systems and apparatus discussed herein, including elements of agent 102 of FIG. 1 and workstation 202 of FIG. 2, may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
receiving a selection of an image from a set of images;
quantifying values of certain quality measures defining an appearance of the selected image;
receiving a modification of the quantified values of the certain quality measures from a user;
mapping the selected image, as modified according to the modified quantified values of the certain quality measures, to a set of imaging parameters of an imaging system using a trained Deep Reinforcement Learning (DRL) agent;
generating a resulting image using the imaging system configured with the set of imaging parameters;
comparing the certain quality measures of the resulting image with the certain quality measures of the selected image as modified according to the modified quantified values of the certain quality measures; and
in response to the comparing, mapping the resulting image to an updated set of imaging parameters of the imaging system using the trained DRL agent.

2. The method of claim 1, further comprising:
generating a new image using the imaging system configured with the updated set of imaging parameters.

3. The method of claim 1, further comprising:
repeating the generating, the comparing, and the mapping the resulting image to the updated set of imaging parameters using the respective updated set of imaging parameters as the set of imaging parameters until the comparing satisfies a threshold.

4. The method of claim 1, wherein comparing the certain quality measures of the resulting image with the certain quality measures of the selected image as modified according to the modification of the certain quality measures comprises:
quantifying values of the certain quality measures for the resulting image; and
comparing the quantified values of the certain quality measures for the resulting image with the certain quality measures of the selected image as modified according to the modified quantified values of the certain quality measures.

5. The method of claim 1, further comprising:
determining the certain quality measures from a set of quality measures for one or more users based on actions of the one or more users on one or more given images using a deep inverse reinforcement learning (DIRL) based method.

6. The method of claim 5, further comprising:
quantifying the values of the set of quality measures for the one or more given images using a trained deep learning based method.

7. The method of claim 1, wherein the one or more quality measures include at least one of sharpness, fuzziness, blurring, noise, dynamic range, contrast, smoothness, and brightness.

8. The method of claim 1, further comprising:
continually monitoring a subject being imaged; and
mapping the selected image, as modified according to the modified quantified values of the certain quality measures, to another updated set of imaging parameters of the imaging system using the trained DRL agent based on the monitoring.

9. An apparatus comprising:
means for receiving a selection of an image from a set of images;
means for quantifying values of certain quality measures defining an appearance of the selected image;
means for receiving a modification of the quantified values of the certain quality measures from a user;
means for mapping the selected image, as modified according to the modified quantified values of the certain quality measures, to a set of imaging parameters of an imaging system using a trained Deep Reinforcement Learning (DRL) agent;
means for generating a resulting image using the imaging system configured with the set of imaging parameters;
means for comparing the certain quality measures of the resulting image with the certain quality measures of the selected image as modified according to the modified quantified values of the certain quality measures; and
in response to the comparing, means for mapping the resulting image to an updated set of imaging parameters of the imaging system using the trained DRL agent.

10. The apparatus of claim 9, further comprising:
means for generating a new image using the imaging system configured with the updated set of imaging parameters.

11. The apparatus of claim 9, further comprising:
means for repeating the generating, the comparing, and the mapping the resulting image to the updated set of imaging parameters using the respective updated set of imaging parameters as the set of imaging parameters until the comparing satisfies a threshold.

12. The apparatus of claim 9, wherein the means for comparing the certain quality measures of the resulting image with the certain quality measures of the selected image as modified according to the modification of the certain quality measures comprises:
  means for quantifying values of the certain quality measures for the resulting image; and
  means for comparing the quantified values of the certain quality measures for the resulting image with the certain quality measures of the selected image as modified according to the modified quantified values of the certain quality measures.

13. A non-transitory computer readable medium storing computer program instructions, the computer program instructions when executed by a processor cause the processor to perform operations comprising:
  receiving a selection of an image from a set of images;
  quantifying values of certain quality measures defining an appearance of the selected image;
  receiving a modification of the quantified values of the certain quality measures from a user;
  mapping the selected image, as modified according to the modified quantified values of the certain quality measures, to a set of imaging parameters of an imaging system using a trained Deep Reinforcement Learning (DRL) agent;
  generating a resulting image using the imaging system configured with the set of imaging parameters;
  comparing the certain quality measures of the resulting image with the certain quality measures of the selected image as modified according to the modified quantified values of the certain quality measures; and
  in response to the comparing, mapping the resulting image to an updated set of imaging parameters of the imaging system using the trained DRL agent.

14. The non-transitory computer readable medium of claim 13, the operations further comprising:
  generating a new image using the imaging system configured with the updated set of imaging parameters.

15. The non-transitory computer readable medium of claim 13, further comprising:
  determining the certain quality measures from a set of quality measures for one or more users based on actions of the one or more users on one or more given images using a deep inverse reinforcement learning (DIRL) based method.

16. The non-transitory computer readable medium of claim 15, further comprising:
  quantifying the values of the set of quality measures for the one or more given images using a trained deep learning based method.

17. The non-transitory computer readable medium of claim 13, wherein the one or more quality measures include at least one of sharpness, fuzziness, blurring, noise, dynamic range, contrast, smoothness, and brightness.

18. The non-transitory computer readable medium of claim 13, further comprising:
  continually monitoring a subject being imaged; and
  mapping the selected image, as modified according to the modified quantified values of the certain quality measures, to another updated set of imaging parameters of the imaging system using the trained DRL agent based on the monitoring.

19. The method of claim 1, wherein the set of imaging parameters of the imaging system comprises at least one of repetition time, echo time, and energy level.

20. The apparatus of claim 9, wherein the set of imaging parameters of the imaging system comprises at least one of repetition time, echo time, and energy level.

* * * * *